United States Patent
Jung, Jr.

(10) Patent No.: US 12,274,482 B2
(45) Date of Patent: Apr. 15, 2025

(54) CRYOBALLOON HAVING GREATER SIZE ADJUSTABILITY AT LOWER OPERATING PRESSURES

(71) Applicant: Boston Scientific Scimed Inc, Maple Grove, MN (US)

(72) Inventor: Eugene J. Jung, Jr., San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 976 days.

(21) Appl. No.: 16/810,339

(22) Filed: Mar. 5, 2020

(65) Prior Publication Data
US 2020/0197067 A1    Jun. 25, 2020

Related U.S. Application Data

(63) Continuation of application No. PCT/US2018/040908, filed on Jul. 5, 2018.
(Continued)

(51) Int. Cl.
*A61B 18/02* (2006.01)
*A61B 18/00* (2006.01)
(Continued)

(52) U.S. Cl.
CPC ........... *A61B 18/02* (2013.01); *A61L 29/049* (2013.01); *A61M 25/09* (2013.01);
(Continued)

(58) Field of Classification Search
None
See application file for complete search history.

(56) References Cited

U.S. PATENT DOCUMENTS

| 6,544,224 B1 | 4/2003 | Steese-Bradley |
| 9,414,878 B1 | 8/2016 | Wu et al. |
| | (Continued) | |

FOREIGN PATENT DOCUMENTS

| JP | 10-087985 A | 4/1998 |
| JP | 2013-146505 A | 8/2013 |
| | (Continued) | |

OTHER PUBLICATIONS

International Search Report and Written Opinion received for PCT Patent Application No. PCT/US2018/040908, mailed on Nov. 21, 2018, 9 pages.

*Primary Examiner* — Ronald Hupczey, Jr.
(74) *Attorney, Agent, or Firm* — Nelson Mullins Riley & Scarborough LLP

(57) ABSTRACT

A balloon catheter for an intravascular catheter system includes a cryogenic balloon that is formed from a blend of polyurethane and polyamide block copolymer. The percentages of polyurethane and polyamide block copolymer can vary. For example, the cryogenic balloon can be formed from greater than 50% polyurethane and less than 50% polyamide block copolymer; greater than 75% polyurethane and less than 25% polyamide block copolymer; or approximately 85% polyurethane and approximately 15% polyamide block copolymer. Additionally, a ratio of a change in inflation pressure (in psi) to a change in outer diameter (in mm) of the cryogenic balloon, and a ratio of outer diameter (in mm) of the cryogenic balloon to inflation pressure (in psig) can be varied to form the desired cryogenic balloon.

12 Claims, 3 Drawing Sheets

Related U.S. Application Data

(60) Provisional application No. 62/555,200, filed on Sep. 7, 2017.

(51) Int. Cl.
*A61B 90/00* (2016.01)
*A61L 29/04* (2006.01)
*A61M 25/09* (2006.01)

(52) U.S. Cl.
CPC .......... *A61B 2018/0022* (2013.01); *A61B 2018/00375* (2013.01); *A61B 2018/00577* (2013.01); *A61B 2018/0212* (2013.01); *A61B 2090/065* (2016.02)

(56) References Cited

U.S. PATENT DOCUMENTS

| | | |
|---|---|---|
| 2002/0053349 A1 | 5/2002 | Anderson et al. |
| 2002/0082553 A1* | 6/2002 | Duchamp ......... A61M 25/1034 604/103.06 |
| 2006/0008606 A1 | 1/2006 | Horn et al. |
| 2007/0167973 A1* | 7/2007 | Stupecky .............. A61M 25/10 264/150 |
| 2007/0197961 A1 | 8/2007 | Wang et al. |
| 2008/0051818 A1 | 2/2008 | Phan et al. |
| 2014/0358136 A1 | 12/2014 | Kelly et al. |
| 2018/0140807 A1* | 5/2018 | Herrera .............. A61M 25/1011 |

FOREIGN PATENT DOCUMENTS

| | | |
|---|---|---|
| JP | 2018-516660 A | 6/2018 |
| WO | 2016/186964 A1 | 11/2016 |
| WO | 2017/106698 A1 | 6/2017 |

\* cited by examiner

| Balloon Material | Diameter @ 2.5psig | Diameter @ 7.5psig | Difference |
|---|---|---|---|
| Balloon 1 Polymer Blend 85% Pellethane 15% Pebax | 28.8mm | 33.4mm | 4.6mm |
| Balloon 2 Pellethane | 25.0mm | 32.9mm | 7.9mm |
| Balloon 3 Pebax 6333D | 28.7mm | 29.9mm | 1.2mm |

FIG. 3

CRYOBALLOON HAVING GREATER SIZE ADJUSTABILITY AT LOWER OPERATING PRESSURES

CROSS-REFERENCE TO RELATED APPLICATION

This application is a continuation of International Application No. PCT/US18/40908, with an international filing date of Jul. 5, 2018, which claims priority to U.S. Provisional Application Ser. No. 62/555,200, filed on Sep. 7, 2017, and entitled "CRYOBALLOON HAVING GREATER SIZE ADJUSTABILITY AT LOWER OPERATING PRESSURES". As far as permitted, the contents of International Application No. PCT/US18/40908 and U.S. Provisional Application Ser. No. 62/555,200 are incorporated in their entirety herein by reference.

TECHNICAL FIELD

The present disclosure relates to medical devices and methods for ablating cardiac tissue. More specifically, the invention relates to cryoablation catheters for treating cardiac arrythmias.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few. In particular, catheter ablation involves delivering ablative energy to tissue inside the heart to block aberrant electrical activity from depolarizing heart muscle cells out of synchrony with the heart's normal conduction pattern. The procedure is performed by positioning the tip of an energy delivery catheter adjacent to diseased or targeted tissue in the heart. The energy delivery component of the system is typically at or near the most distal (i.e. farthest from the user or operator) portion of the catheter, and often at the tip of the catheter. [0003] Various forms of energy can be used to ablate diseased heart tissue. These can include cryoablation procedures which use cryogenic fluid within cryoballoons (also sometimes referred to herein as "cryogenic balloons" or "balloon catheters"), radio frequency (RF), ultrasound and laser energy, to name a few. During a cryoablation procedure, with the aid of a guide wire, the distal tip of the catheter is positioned adjacent to targeted cardiac tissue, at which time energy is delivered to create tissue necrosis, rendering the ablated tissue incapable of conducting electrical signals. The dose of energy delivered is a critical factor in increasing the likelihood that the treated tissue is permanently incapable of conduction. At the same time, delicate collateral tissue, such as the esophagus, the bronchus, and the phrenic nerve surrounding the ablation zone can be damaged and can lead to undesired complications. Thus, the operator must finely balance delivering therapeutic levels of energy to achieve intended tissue necrosis while avoiding excessive energy leading to collateral tissue injury.

Atrial fibrillation (AF) is one of the most common arrhythmias treated using catheter ablation. AF is typically treated by pulmonary vein isolation, a procedure that removes unusual electrical conductivity in the pulmonary vein. In the earliest stages of the disease, paroxysmal AF, the treatment strategy involves isolating the pulmonary veins from the left atrial chamber. Cryoballoon ablation procedures to treat atrial fibrillation have increased in use in the last several years. In part, this stems from the ease of use, shorter procedure times and improved patient outcomes that are possible through the use of cryoballoon ablation procedures. Despite these advantages, there remains needed improvement to further improve patient outcomes and to better facilitate real-time physiological monitoring of tissue to optimally titrate energy to perform both reversible "ice mapping" and permanent tissue ablation.

The objective of any device for the treatment of AF is to achieve isolation in all, not just some, of the pulmonary veins. Also, it is understood that complete occlusion of each pulmonary vein with the cryogenic balloon is required for adequate antral ablation and electrical isolation. Without pulmonary vein occlusion, blood flow over the balloon during ablation decreases the likelihood of sufficient lesion formation. In order to achieve pulmonary vein occlusion with a balloon, the balloon outer diameter (also sometimes referred to herein as the "balloon diameter" or the "outer diameter") should ideally be a little larger than the opening, or ostium, of the pulmonary vein. If the balloon is too small, there can be gaps between the balloon and the pulmonary vein, enabling blood to flow through the gaps. Conversely, if the balloon is too large, a distal surface of the balloon may be improperly positioned due to the presence of other anatomical features so that the balloon is not sealed tightly against the ostium of the pulmonary vein.

In intravascular catheter systems such as cryogenic balloon catheter systems, it is common that two balloons are used (although a single balloon may also be used) to create a cryo-chamber near the distal tip of the catheter. The balloons are configured such that there is an inner balloon that receives the cryogenic cooling fluid and an outer balloon that surrounds the inner balloon. The outer balloon acts as part of a safety system to capture the cryogenic cooling fluid in the event of a leak from the inner balloon. In a typical cryogenic balloon catheter system, the cryogenic balloons are relatively non-compliant and are of a single diameter when in the ablation mode. Thus, current cryogenic balloons are limited in utility because the diameter of the inflated cryogenic balloon cannot be changed during ablation. However, human pulmonary vein diameter and shape can vary significantly within and between patients. Consequently, current cryogenic balloons offer an all or nothing capability in treating pulmonary veins in pulmonary vein isolation procedures.

Thus, a cryogenic balloon that is adjustable in size and shape so as to be more adaptable to common variations in human pulmonary vein diameter and shape is desired in order to better achieve pulmonary vein occlusion and isolation in a greater percentage of patients treated. Furthermore, a cryogenic balloon is needed that has a relatively wide-ranging diameter which can be determined by an operator based primarily or solely upon pressure within the cryoballoon.

In a cryogenic balloon catheter system, the balloon operating pressure (also sometimes referred to herein as the "balloon pressure" or the "inflation pressure"), the balloon diameter, and the energy flow rate through the balloon catheter are inter-related. A cryogenic balloon catheter system is unique in that the inflation pressure is a consequence of the refrigerant flow rate through the balloon catheter. The flow rate of the refrigerant determines the amount of energy delivered to the treatment site, such as the targeted cardiac tissue of the heart. The amount of energy delivered to the treatment site must be accurate and precise to increase the likelihood of an adequate therapeutic effect, such as obtaining pulmonary vein isolation, but also freedom from collateral tissue injury, which can result from excessive energy delivery. Thus, a relatively narrow therapeutic dose window is desired to attain better procedure outcomes. Ideally, a small increase in inflation pressure should correspond to a specific, yet clinically meaningful increase in balloon diameter while remaining within an optimal dose window.

Additionally, in some applications, it is desirable that the change from one balloon outer diameter to another using the same balloon should be achievable multiple times in a predictable fashion. An ideal variable-diameter balloon would offer a useful range of diameters achievable during ablation within a relatively narrow range of inflation pressures constrained by the need for providing a prescribed amount of cryoenergy delivered into the body of the patient by a cryoablation balloon catheter. This feature would enable the operator to move the balloon catheter from one pulmonary vein to the next, change the outer diameter of the balloon to occlude the pulmonary vein, apply therapy to achieve a successful outcome, and then move to the next pulmonary vein to repeat the process.

SUMMARY

The present invention is directed toward a balloon catheter for an intravascular catheter system. In various embodiments, the balloon catheter includes a cryogenic balloon that is formed from a blend of polyurethane and polyamide block copolymer.

In some embodiments, the cryogenic balloon is formed from greater than 50% polyurethane and less than 50% polyamide block copolymer. In certain such embodiments, the cryogenic balloon is formed from greater than 75% polyurethane and less than 25% polyamide block copolymer. In other such embodiments, the cryogenic balloon is formed from approximately 85% polyurethane and approximately 15% polyamide block copolymer.

Additionally, in certain embodiments, a ratio of a change in inflation pressure (in psi) to a change in outer diameter (in mm) of the cryogenic balloon is less than approximately 10:1. In other embodiments, a ratio of a change in inflation pressure (in psi) to a change in outer diameter (in mm) of the cryogenic balloon is less than approximately 8:1. In still other embodiments, a ratio of a change in inflation pressure (in psi) to a change in outer diameter (in mm) of the cryogenic balloon is less than approximately 6:1. In yet other embodiments, a ratio of a change in inflation pressure (in psi) to a change in outer diameter (in mm) of the cryogenic balloon is less than approximately 4:1. In still other embodiments, a ratio of a change in inflation pressure (in psi) to a change in outer diameter (in mm) of the cryogenic balloon is less than approximately 2:1. In still yet other embodiments, a ratio of a change in inflation pressure (in psi) to a change in outer diameter (in mm) of the cryogenic balloon is less than approximately 1:1. In even other embodiments, a ratio of a change in inflation pressure (in psi) to a change in outer diameter (in mm) of the cryogenic balloon is less than approximately 1:2.

Further, in some embodiments, a ratio of outer diameter (in mm) of the cryogenic balloon to inflation pressure (in psig) is greater than approximately 20:1. In other embodiments, a ratio of outer diameter (in mm) of the cryogenic balloon to inflation pressure (in psig) is greater than approximately 15:1. In still other embodiments, a ratio of outer diameter (in mm) of the cryogenic balloon to inflation pressure (in psig) is greater than approximately 10:1. In yet other embodiments, a ratio of outer diameter (in mm) of the cryogenic balloon to inflation pressure (in psig) is greater than approximately 8:1. In other embodiments, a ratio of outer diameter (in mm) of the cryogenic balloon to inflation pressure (in psig) is greater than approximately 5:1. In still yet other embodiments, a ratio of outer diameter (in mm) of the cryogenic balloon to inflation pressure (in psig) is greater than approximately 3:1.

Additionally, in certain embodiments, an outer diameter of the cryogenic balloon changes by at least 1 mm with a change in inflation pressure of not greater than 5 psi. In other embodiments, an outer diameter of the cryogenic balloon changes by at least 2 mm with a change in inflation pressure of not greater than 5 psi. In still other embodiments, an outer diameter of the cryogenic balloon changes by at least 3 mm with a change in inflation pressure of not greater than 5 psi. In yet other embodiments, an outer diameter of the cryogenic balloon changes by at least 4 mm with a change in inflation pressure of not greater than 5 psi. In still yet other embodiments, an outer diameter of the cryogenic balloon changes by at least 5 mm with a change in inflation pressure of not greater than 5 psi. In such alternative embodiments, the change in inflation pressure of not greater than 5 psi can occur within the range of between approximately 2.5 psig and approximately 7.5 psig.

In another embodiment, the present invention is directed toward a balloon catheter for an intravascular catheter system, the balloon catheter including a cryogenic balloon that is formed from materials having properties such that a ratio of a change in inflation pressure (in psi) to a change in outer diameter (in mm) of the cryogenic balloon is less than approximately 10:1.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3 is a table showing outer diameters of three different balloons usable within the balloon catheter of the intravascular catheter system at different inflation pressures.

Figure 1:
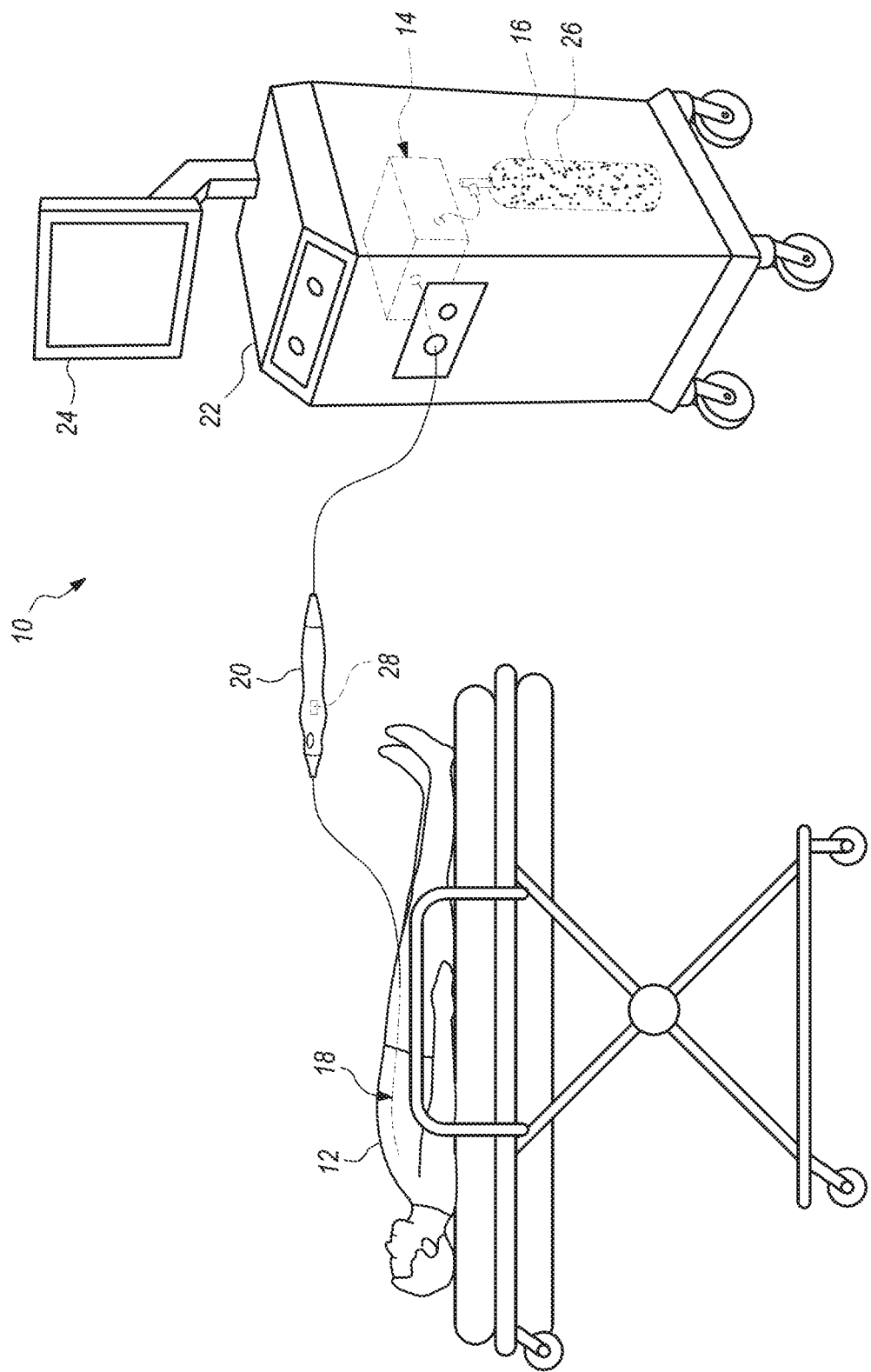
FIG. 1 is a simplified schematic side view illustration of a patient and one embodiment of an intravascular catheter system having features of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Embodiments of the present invention are described herein in the context of a cryogenic balloon for use within an intravascular catheter system. More specifically, in various embodiments, the present invention is directed toward balloon materials, characteristics and dimensions, which can be controlled to provide improve balloon diameter adjustability at different, e.g., lower, inflation pressures.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Although the disclosure provided herein focuses mainly on cryogenics, it is understood that various other forms of energy can be used to ablate diseased heart tissue. These can include radio frequency (RF), ultrasound, pulsed DC electric fields and laser energy, as non-exclusive examples. The present invention is intended to be effective with any or all of these and other forms of energy.

As an overview, with the teachings provided herein regarding the materials, characteristics and dimensions for a cryogenic balloon of an intravascular catheter system, cryo-energy and cryoablation can be improved by substantially repeatable cryoballoon balloon diameter changes of several millimeters at relatively low operating pressures.

FIG. 1 is a simplified schematic side view illustration of an embodiment of a medical device 10 for use with a patient 12, which can be a human being or an animal. Although the specific medical device 10 illustrated and described herein pertains to and refers to an intravascular catheter system 10 such as a cryogenic balloon catheter system, it is understood and appreciated that other types of medical devices 10 or systems can equally benefit by the teachings provided herein. For example, in certain non-exclusive alternative embodiments, the present invention can be equally applicable for use with any suitable types of ablation systems and/or any suitable types of catheter systems. Thus, the specific reference herein to use as part of an intravascular catheter system is not intended to be limiting in any manner.

The design of the intravascular catheter system 10 can be varied. In certain embodiments, such as the embodiment illustrated in FIG. 1, the intravascular catheter system 10 can include one or more of a control system 14 (illustrated in phantom), a fluid source 16 (illustrated in phantom), a balloon catheter 18, a handle assembly 20, a control console 22, and a graphical display 24.

It is understood that although FIG. 1 illustrates the structures of the intravascular catheter system 10 in a particular position, sequence and/or order, these structures can be located in any suitably different position, sequence and/or order than that illustrated in FIG. 1. It is also understood that the intravascular catheter system 10 can include fewer or additional components than those specifically illustrated and described herein.

In various embodiments, the control system 14 is configured to monitor and control various processes of the ablation procedure. More specifically, the control system 14 can monitor and control release and/or retrieval of a cooling fluid 26 (e.g., a cryogenic fluid) to and/or from the balloon catheter 18. The control system 14 can also control various structures that are responsible for maintaining and/or adjusting a flow rate and/or pressure of the cryogenic fluid 26 that is released to the balloon catheter 18 during the cryoablation procedure. In such embodiments, the intravascular catheter system 10 delivers ablative energy in the form of cryogenic fluid 26 to cardiac tissue of the patient 12 to create tissue necrosis, rendering the ablated tissue incapable of conducting electrical signals. Additionally, in various embodiments, the control system 14 can control activation and/or deactivation of one or more other processes of the balloon catheter 18. Further, or in the alternative, the control system 14 can receive data and/or other information (hereinafter sometimes referred to as "sensor output") from various structures within the intravascular catheter system 10. In some embodiments, the control system 14 can receive, monitor, assimilate and/or integrate the sensor output and/or any other data or information received from any structure within the intravascular catheter system 10 in order to control the operation of the balloon catheter 18. As provided herein, in various embodiments, the control system 14 can initiate and/or terminate the flow of cryogenic fluid 26 to the balloon catheter 18 based on the sensor output. Still further, or in the alternative, the control system 14 can control positioning of portions of the balloon catheter 18 within the body of the patient 12, and/or can control any other suitable functions of the balloon catheter 18.

Additionally, in some embodiments, the control system 14 can include, incorporate or utilize a pressure sensor 28 that can be configured to sense a contact pressure between the balloon and the targeted vein to be occluded. As provided herein, the pressure sensor 28 can be utilized to better ensure that a desired, predetermined contact force or contact pressure is generated between the balloon and the targeted vein to achieve the desired vein occlusion. It is appreciated that the pressure sensor 28 can be positioned in any suitable manner within the intravascular catheter system 10.

The fluid source 16 contains the cryogenic fluid 26, which is delivered to the balloon catheter 18 with or without input from the control system 14 during a cryoablation procedure. Once the ablation procedure has initiated, the cryogenic fluid 26 can be delivered to the balloon catheter 18 and the resulting gas, after a phase change, can be retrieved from the balloon catheter 18, and can either be vented or otherwise discarded as exhaust. Additionally, the type of cryogenic fluid 26 that is used during the cryoablation procedure can vary. In one non-exclusive embodiment, the cryogenic fluid 26 can include liquid nitrous oxide. However, any other suitable cryogenic fluid 26 can be used. For example, in one non-exclusive alternative embodiment, the cryogenic fluid 26 can include liquid nitrogen.

The design of the balloon catheter 18 can be varied to suit the specific design requirements of the intravascular catheter system 10. As shown, the balloon catheter 18 is configured to be inserted into the body of the patient 12 during the cryoablation procedure, i.e. during use of the intravascular catheter system 10. In one embodiment, the balloon catheter 18 can be positioned within the body of the patient 12 using the control system 14. Stated in another manner, the control system 14 can control positioning of the balloon catheter 18 within the body of the patient 12. Alternatively, the balloon catheter 18 can be manually positioned within the body of the patient 12 by a healthcare professional (also referred to herein as an "operator"). As used herein, a healthcare professional and/or an operator can include a physician, a physician's assistant, a nurse and/or any other suitable person and/or individual. In certain embodiments, the balloon catheter 18 is positioned within the body of the patient 12 utilizing at least a portion of the sensor output that is received by the control system 14. For example, in various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12 to ensure that the balloon catheter 18 is properly positioned relative to targeted cardiac tissue (not shown). While specific reference is made herein to the balloon catheter 18, as noted above, it is understood that any suitable type of medical device and/or catheter may be used.

The handle assembly 20 is handled and used by the operator to operate, position and control the balloon catheter 18. The design and specific features of the handle assembly 20 can vary to suit the design requirements of the intravascular catheter system 10. In the embodiment illustrated in FIG. 1, the handle assembly 20 is separate from, but in electrical and/or fluid communication with the control system 14, the fluid source 16, and the graphical display 24. In some embodiments, the handle assembly 20 can integrate and/or include at least a portion of the control system 14, e.g., the pressure sensor 28, within an interior of the handle assembly 20. It is understood that the handle assembly 20 can include fewer or additional components than those specifically illustrated and described herein.

In various embodiments, the handle assembly 20 can be used by the operator to initiate and/or terminate the cryoablation process, e.g., to start the flow of the cryogenic fluid 26 to the balloon catheter 18 in order to ablate certain targeted heart tissue of the patient 12. In certain embodiments, the control system 14 can override use of the handle assembly 20 by the operator. Stated in another manner, in some embodiments, based at least in part on the sensor output, the control system 14 can terminate the cryoablation process without the operator using the handle assembly 20 to do so.

The control console 22 is coupled to the balloon catheter 18 and the handle assembly 20. Additionally, in the embodiment illustrated in FIG. 1, the control console 22 includes at least a portion of the control system 14, the fluid source 16, and the graphical display 24. However, in alternative embodiments, the control console 22 can contain additional structures not shown or described herein. Still alternatively, the control console 22 may not include various structures that are illustrated within the control console 22 in FIG. 1. For example, in certain nonexclusive alternative embodiments, the control console 22 does not include the graphical display 24.

In various embodiments, the graphical display 24 is electrically connected to the control system 14. Additionally, the graphical display 24 provides the operator of the intravascular catheter system 10 with information and data that can be used before, during and after the cryoablation procedure. For example, the graphical display 24 can provide the operator with information based on the sensor output and any other relevant information that can be used before, during and after the cryoablation procedure. The specifics of the graphical display 24 can vary depending upon the design requirements of the intravascular catheter system 10, or the specific needs, specifications and/or desires of the operator.

In one embodiment, the graphical display 24 can provide static visual data and/or information to the operator. In addition, or in the alternative, the graphical display 24 can provide dynamic visual data and/or information to the operator, such as video data or any other data that changes over time, e.g., during an ablation procedure. Further, in various embodiments, the graphical display 24 can include one or more colors, different sizes, varying brightness, etc., that may act as alerts to the operator. Additionally, or in the alternative, the graphical display 24 can provide audio data or information to the operator.

Figure 2:
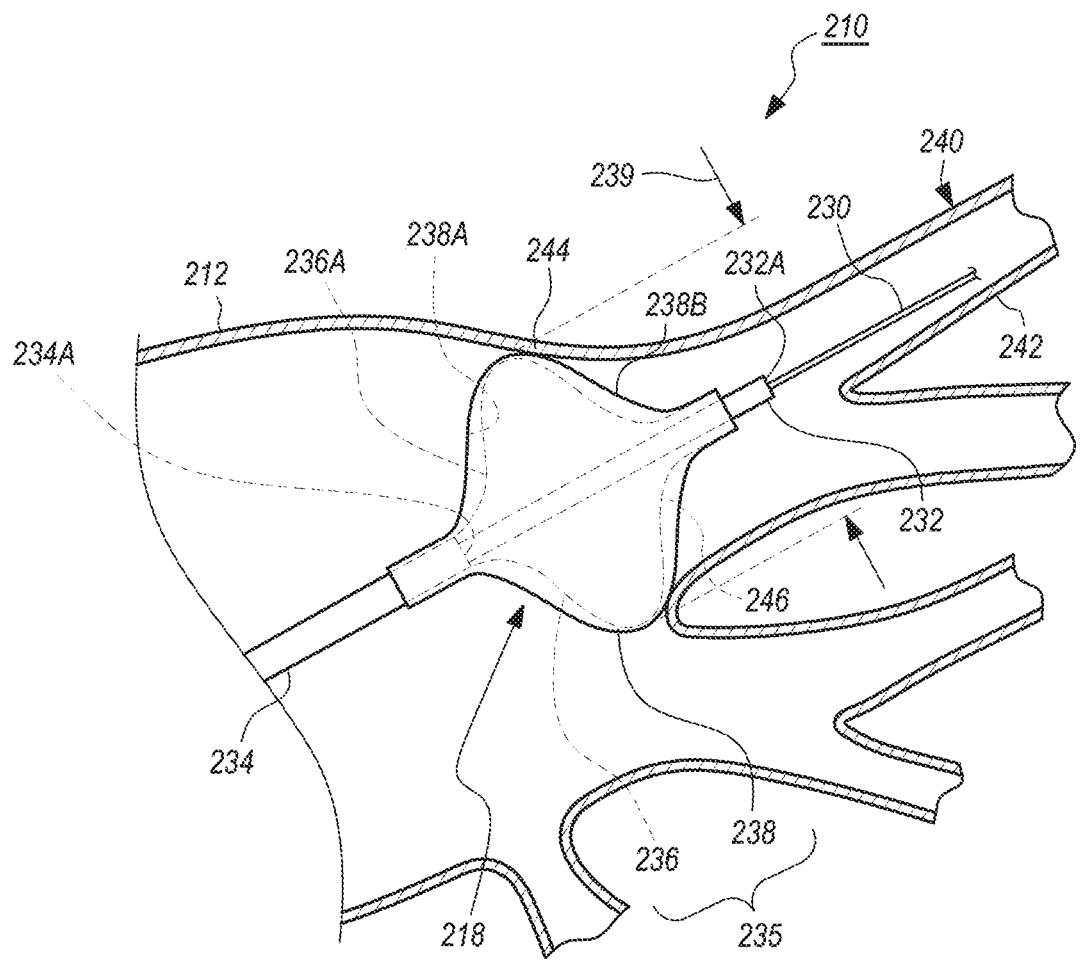
FIG. 2 is a simplified schematic side view illustration of a portion of the patient and a portion of an embodiment of the intravascular catheter system including a balloon catheter.

FIG. 2 is a simplified schematic side view illustration of a portion of the patient 212 and a portion of one embodiment of the intravascular catheter system 210. As shown in FIG. 2, in this embodiment, the intravascular catheter system 210 includes a balloon catheter 218. In certain embodiments, the balloon catheter 218 can be a low-profile, anatomy-conforming balloon catheter for cryogenically or thermally ablating tissue surrounding one or more pulmonary veins 242 for the treatment of atrial fibrillation in order to improve outcomes and procedural safety. Certain embodiments of the intravascular catheter system 210 can also or alternatively provide a structure able to be delivered through a small profile delivery device.

The design of the balloon catheter 218 can be varied to suit the design requirements of the intravascular catheter system 210. In the embodiment illustrated in FIG. 2, the balloon catheter 218 includes one or more of a guidewire 230, a guidewire lumen 232, a catheter shaft 234, and a balloon assembly 235 including an inner inflatable balloon 236 (sometimes referred to herein as a "first inflatable balloon", an "inner balloon" or a "first balloon") and an outer inflatable balloon 238 (sometimes referred to herein as a "second inflatable balloon", an "outer balloon" or a "second balloon"). As used herein, it is recognized that either balloon 236, 238 can be described as the first balloon or the second balloon. Further, the inner balloon 236 and/or the outer balloon 238 can also be referred to generally as a "cryogenic balloon". For example, in certain applications, the inner balloon 236 can be the cryogenic balloon that is manufactured with the materials, characteristics and dimensions as described in detail herein. Alternatively, the balloon catheter 218 can be configured to include only a single balloon.

Additionally, it is understood that the balloon catheter 218 can include other structures as well. However, for the sake of clarity, these other structures have been omitted from the Figures. Further, as shown in FIG. 2, the balloon assembly 235, i.e. the inner balloon 236 and/or the outer balloon 238, has an outer diameter 239.

As shown in the embodiment illustrated in FIG. 2, the balloon catheter 218 is configured to be positioned within the circulatory system 240 of the patient 212. The guidewire 230 and guidewire lumen 232 are inserted into a pulmonary vein 242 of the patient 212, and the catheter shaft 234 and the balloons 236, 238 are moved along the guidewire 230 and/or the guidewire lumen 232 to near an ostium 244 of the pulmonary vein 242.

Additionally, as shown, the guidewire lumen 232 encircles at least a portion of the guidewire 230. During use, the guidewire 230 is inserted into the guidewire lumen 232 and can course through the guidewire lumen 232 and extend out of a distal end 232A of the guidewire lumen 232. In various embodiments, the guidewire 230 can also include a mapping catheter (not shown) that maps electrocardiograms in the heart, and/or can provide information needed to position at least portions of the balloon catheter 218 within the patient 212.

As illustrated in this embodiment, the inner balloon 236 is positioned substantially, if not completely, within the outer balloon 238. Additionally, in some embodiments, one end of the inner balloon 236 is bonded to a distal end 234A of the catheter shaft 234, and the other end of the inner balloon 236 is bonded near the distal end 232A of the guidewire lumen 232. Further, one end of the outer balloon 238 may be bonded to a neck of the inner balloon 236 or to the distal end 234A of the catheter shaft 234, and the other end of the outer balloon 238 may be bonded to the guidewire lumen 232. Additionally, it is further appreciated that in embodiments that include only a single balloon, the balloon can be secured to the catheter shaft 234 and the guidewire lumen 232 in a similar manner. Alternatively, the balloons 236, 238 can be secured to other suitable structures.

It is appreciated that a variety of bonding techniques can be used and include heat-bonding and adhesive-bonding. For example, in at least some embodiments, the bonding can be accomplished using thermal fusing techniques. These techniques are possible because of the use of materials in both the inner balloon 236 and the outer balloon 238 to enhance compatibility for fusing while preserving the respective functional requirements of each balloon 236, 238, which can be rather different from one another. In such embodiments, each of the balloons 236, 238 can be heat-bonded, e.g., to the catheter shaft 234 and/or the guidewire lumen 232, to achieve a small diameter, using a laser or clam shell heated die set, for example. To facilitate a heat-bond, the catheter shaft 234, the guidewire lumen 232 and the balloons 236, 238 can be chosen so they are compatible for heat-bonding. Alternatively, as noted, the balloons 236, 238 can be adhesive-bonded to the catheter shaft 234 and/or the guidewire lumen 232.

During use, the inner balloon 236 can be partially or fully inflated so that at least a portion of the inner balloon 236 expands against at least a portion of the outer balloon 238. Stated in another manner, during use of the balloon catheter 218, at least a portion of an outer surface 236A of the inner balloon 236 expands and is positioned substantially directly against a portion of an inner surface 238A of the outer balloon 238. As such, when the inner balloon 236 has been fully inflated, the inner balloon 236 and the outer balloon 238 have a somewhat similar physical footprint. Thus, since the inner balloon 236 and the outer balloon 238 have a similar physical footprint, any of the inner balloon 236, the outer balloon 238 and/or the balloon assembly 235 can be said to include the outer diameter 239.

At certain times during usage of the intravascular catheter system 210, the inner balloon 236 and the outer balloon 238 define an inter-balloon space 246, or gap, between the balloons 236, 238. The inter-balloon space 246 is illustrated between the inner balloon 236 and the outer balloon 238 in FIG. 2 for clarity, although it is understood that at certain times during usage of the intravascular catheter system 210, the inter-balloon space 246 has very little or no volume. As provided herein, once the inner balloon 236 is sufficiently inflated, an outer surface 238B of the outer balloon 238 can then be positioned within the circulatory system 240 of the patient 212 to abut and/or substantially form a seal with the ostium 244 of the pulmonary vein 242 to be treated. In particular, during use, it is generally desired that the outer diameter 239 of the balloon assembly 235 be slightly larger than the diameter of the pulmonary vein 242 to best enable occlusion of the pulmonary vein 242. As noted above, having a balloon assembly 235 with an outer diameter 239 that is either too small or too large can create problems that inhibit the ability to achieve the desired occlusion of the pulmonary vein 242.

As provided herein, one way to treat a wider range of human anatomy is to better size the balloons 236, 238 of the balloon catheter 218 to match the diameter of the pulmonary vein 242. In general, it is the object of the balloon catheter 218 to seal the pulmonary vein 242 so that blood flow is occluded. Only when occlusion is achieved does the cryothermic energy, e.g., of the cryogenic fluid 26 (illustrated in FIG. 1), cause tissue necrosis which, in turn, provides for electrically blocking aberrant electrical signals that trigger atrial fibrillation. Unfortunately, as noted above, human anatomy varies, and the diameter of pulmonary veins varies within a given patient as well as between patients. For example, in different patients, as well as within a single patient, the anatomy of the human pulmonary vein 242 can vary from less than approximately twelve millimeters (12 mm) in diameter to greater than thirty millimeters (30 mm) in diameter.

In various embodiments, the variety of pulmonary vein diameters can be treated by providing a balloon catheter 218 that includes balloons 236, 238 that are selectively adjustable to provide a range of available outer diameters 239. An intravascular catheter system 210 that varies the outer diameter 239 of the balloon assembly 235 can preclude the need to utilize multiple balloon catheters to successfully complete a procedure. The use of multiple balloon catheters increases procedure time, risk of injury to the patient 212, and procedural cost. Thus, the balloon catheter 218 disclosed herein includes a balloon assembly 235, i.e. an inner balloon 236 and/or an outer balloon 238, that can vary the outer diameter 239 predictably and reliably over the course of numerous inflation, deflation, and ablation cycles. This attribute enables the operator to move the balloon catheter 218 from one pulmonary vein 242 to the next, change the outer diameter 239 of the balloon assembly 235 to occlude the pulmonary vein 242, apply therapy to achieve successful outcomes, then move to the next pulmonary vein 242 and repeat the process. Ideally, this process of advancing the balloon catheter 218 to a pulmonary vein 242, adjusting the outer diameter 239 to occlude the pulmonary vein 242, and applying therapy, can be repeated any number of times as the operator desires to complete the procedure. In effect, the balloon assembly 235, along with the remainder of the intravascular catheter system 210, offers the operator the capability to adjust the outer diameter 239 of the balloon assembly 235 to better seal the pulmonary vein 242 while effectively keeping the energy dose (balloon pressure or inflation pressure) within a narrow, safe, and effective therapeutic window.

As noted above, the operating balloon pressure or inflation pressure of the balloon assembly 235, the outer diameter 239 of the balloon assembly 235, and the energy flow rate through the balloon catheter 218 are inter-related. During use of the intravascular catheter system 210, the inflation pressure is a consequence of the flow rate of the cryogenic fluid 26 (illustrated in FIG. 1) through the balloon catheter 218. The flow rate of the cryogenic fluid 26 determines the amount of energy delivered to the treatment site, such as the targeted cardiac tissue of the heart. The amount of energy delivered to the treatment site should be accurate and precise to increase the likelihood of adequate therapeutic effect, including obtaining isolation of the pulmonary vein 242, and freedom from collateral tissue injury, which can result from excessive energy delivery. Importantly, a relatively narrow therapeutic dose window is required to increase the likelihood of improved patient outcomes. Thus, it follows that a small increase in inflation pressure corresponds to a specific, yet clinically meaningful increase in the outer diameter 239 of the balloon assembly 235, while remaining within a narrow dose window. It may be advantageous to increase the energy delivered as the balloon assembly 235 is inflated to a larger outer diameter 239 to offset heat loss resulting from larger surface area of the larger outer diameter 239.

Additionally, as provided herein, the balloons 236, 238 can be designed to include certain performance parameters. For example, in various embodiments, performance parameters of the balloons 236, 238 and/or the balloon assembly 235 can include one or more of (i) a relatively predictable outer diameter-pressure curve, (ii) balloons 236, 238 having a relatively thin wall, (iii) an ability to expand to a desired operating range of outer diameters 239 at relatively low inflation pressures and/or with small pressure changes, (iv) a relatively high burst pressure for the balloons 236, 238 having a given wall thickness, (v) dimensional stability including resistance to shrinkage during sterilization, and/or (vi) other manufacturing processes and resistance against pinholes and other defects in the balloons 236, 238. Additionally, in certain embodiments, the balloons 236, 238 that are ultimately inserted into the body of the patient 212 will have little or no hysteresis so that the operator can inflate the balloons 236, 238 to variable and predictable sizes based on known inflation pressures.

In typical balloons in current use, there is a lack of balloon materials that lend themselves to meet all the performance and safety requirements for a cryogenic balloon and enable a useful range of diameters. For example, non-compliant balloons (described herein as balloons that are typically insensitive to pressure changes, with an inflated diameter that remains within less than approximately 6% of the nominal diameter over the typical operating range of internal pressures) or semi-compliant balloons (described herein as balloons where the inflated diameter changes between approximately 6-12% from the nominal diameter over the typical operating range of internal pressures) in general use typically do not offer a wide enough range to meet the clinical need. Conversely, while compliant balloons (described herein as balloons where the inflated diameter changes greater than approximately 12% from the nominal diameter over the typical operating range of internal pressures) made from very soft polymers expand readily to fit the anatomy, they are plagued by hysteresis and have low burst pressures that fail to offer appropriate levels of safety. [0051] The specific design of and materials used for each of the inner inflatable balloon 236 and the outer inflatable balloon 238 can be varied. For example, in order to meet some or all of the above-noted performance parameters, a polymer capable of being extruded and formed into a thin, homogeneous film can be used. In various embodiments, specialty polymers with engineered properties can be used.

As provided herein, in various embodiments, the inner inflatable balloon 236 can be formed from a specially processed, engineered polymer material or blended polymer materials enabling a very thin wall thickness, e.g. less than approximately 0.0010 inches (25.4 microns). In one embodiment, the wall thickness of the inner inflatable balloon 236 can be between approximately 0.0004 inches (10 microns) and 0.0010 inches (25.4 microns). In another embodiment, the wall thickness of the inner inflatable balloon 236 can be equal to or less than approximately 0.0004 inches (10 microns). In each of these embodiments, the inner inflatable balloon 236 offers durability to withstand multiple ablation cycles while still performing within specifications. The ability of the inner inflatable balloon 236 to be selectively inflated to differing outer diameters 239, using a relatively small change in inflation pressure, enables the operator to use a single device to effectively treat a wider range of pulmonary vein anatomies, which often present with different diameters, sizes and shapes within one patient 212 and also from patient 212 to patient 212. The outer diameter 239 of the inner inflatable balloon 236 described herein can be precisely changed using small incremental changes in inflation pressure, within a range of inflation pressures commonly used for cryoballoon procedures, such as from 2 psig to 15 psig.

In addition to single polymers, blends of polymers can result in a suitable material for use in the inner inflatable balloon 236. For example, some representative materials suitable for the inner inflatable balloon 236 include various grades of polyether block amides (PEBA), which include a copolymer family comprised of rigid polyamide blocks and flexible polyether blocks, such as the commercially available PEBAX® (marketed by Arkema, Colombes, France), or a thermoplastic polyurethane such as Pellathane™ (marketed by Lubrizol). Additionally, or in the alternative, the materials can include PET (polyethylene terephthalate), nylon, polyurethane, and other co-polymers of these materials, as non-exclusive examples. In another embodiment, a polyester block copolymer known in the trade as Hytrel® (DuPont™) is also a suitable material for the inner inflatable balloon 236. Further, the materials may be mixed in varying amounts to fine tune properties of the inner inflatable balloon 236. Other suitable materials can additionally or alternatively be used for the inner inflatable balloon 236, and the foregoing examples of materials used for the inner inflatable balloon 236 are not intended to be limiting in any manner.

Additionally, in order to enable a meaningful change in outer diameter 239 over a relatively small inflation pressure range, the material elasticity must be within a range of properties that facilitates low pressure expansion. One type of polymer that satisfies this criterion has a range of hardness from 90 Shore A to 63 Shore D. Using the processes described herein it is possible that a wider range of Durometers may provide for a variable outer diameter 239.

In one non-exclusive embodiment, the inner inflatable balloon 236 can be made from a mixture of polyurethane, such as Pellethane™ 2363-90A TPU, and PEBAX® 6333, a polyether block amides or polyamide block copolymer. The ratio of polyurethane to the polyamide block copolymer can vary. In one embodiment, the ratio of polyurethane to the polyamide block copolymer can be approximately 15:85 (approximately 15% polyurethane to approximately 85% polyamide block copolymer). More specifically, for example, a Lubrizol Pellathane™ and Arkema PEBAX® in an approximately 15% PEBAX® and approximately 85% Pellathane™ weight mixture provides for one suitable cryoballoon material. The PEBAX® in this application is the grade 6033 although it is also contemplated that the 7033 and 5533 grades can also be used. The Pellathane™ grade is 90 A and like the PEBAX®, other grades could be used. For a single polymer material such as PEBAX® 6333, 5533 or Lubrizol TECOBAX® in hardness grades of 40 Shore D and 47 Shore D are also suitable.

In alternative embodiments, the ratio of polyurethane to the polyamide block copolymer can be different than what was specifically noted above. For example, the ratio of the mixture can be adjusted to approximately 25% polyurethane to approximately 75% polyamide block copolymer. The ratio of the mixture can also be adjusted to approximately 50% of each material. In certain non-exclusive alternative embodiments, the inner inflatable balloon 236 can be formed from greater than 50% polyurethane and less than 50% polyamide block copolymer, greater than 75% polyurethane and less than 25% polyamide block copolymer, or greater than 85% polyurethane and less than 15% polyamide block copolymer. Still alternatively, other ratios of polyurethane to polyamide block copolymer can be used to form the inner inflatable balloon 236. The different ratios are chosen to improve the inflation pressure-outer diameter curve. Further, the balloon tubing can be extruded from a mixture of materials. By mixing two different materials with widely differing polymeric compositions, a balloon of ideal characteristics that is also heat-bondable to the catheter shaft 234 can be formed.

As illustrated, the outer inflatable balloon 238 substantially encircles the inner inflatable balloon 236. In certain embodiments, the outer inflatable balloon 238 can be formed from similar materials and can be formed in a similar manner as the inner inflatable balloon 236. For example, some representative materials suitable for the outer inflatable balloon 238 for this variable-diameter compliant two-balloon system include various grades of polyether block amides (PEBA) such as the commercially available PEBAX®, or a polyurethane such as Pellathane™. Additionally, or in the alternative, the materials can include aliphatic polyether polyurethanes in which carbon atoms are linked in open chains, including paraffins, olefins, and acetylenes. Another suitable material goes by the trade name Tecoflex® (marketed by Lubrizol). Other available polymers from the polyurethane class of thermoplastic polymers with exceptional elongation characteristics are also suitable for use as the outer inflatable balloon 238. Further, the materials may be mixed in varying amounts to fine tune properties of the outer inflatable balloon 238. In order to achieve a homogeneous mixture of different polymer compounds, the blended material can be compounded together using a process to better homogenize the polymer into pellets used in the extrusion process.

A lubricious biocompatible material such as a grease may be inserted between the balloons 236, 238 to enable free expansion of the inner balloon 236 against the constraining outer balloon 238. Other lubricants are contemplated. Alternatively, a lubricious additive may be compounded into either the inner balloon or outer balloon tubing to reduce friction between the two balloons 236, 238 during inflation to better enable predictable and repeatable outer diameters 239 for a given inflation pressure. The lubricant increases the likelihood that the intended outer diameter 239 is achieved at the various inflation pressures defining the working range. The lubricant can also reduce the working pressures, as far as is possible, so that the full working range of outer diameter 239 may be several multiples below the burst pressure of the two-balloon system. For example, a two-balloon compliant balloon system may have an average burst pressure of 30 psi. A working range of inflation pressures such as 2.5 psi to 11 psi ensures that there is a significant margin of safety between the balloon burst pressure and the inflation pressure range needed to provide the full span of outer diameters 239 that the operator may desire.

FIG. 3 is a table showing outer diameters 239 (illustrated in FIG. 2) of three different balloons, e.g., cryogenic balloons or "cryoballoons", usable within the balloon catheter 218 (illustrated in FIG. 2) of the intravascular catheter system 210 (illustrated in FIG. 2) at different inflation pressures. It is appreciated that the balloons being depicted in the table shown in FIG. 3 can be embodiments of the inner balloon 236 (illustrated in FIG. 2). Alternatively, the balloons being depicted in the table shown in FIG. 3 can be embodiments of the outer balloon 238 (illustrated in FIG. 2).

In particular, Balloon 1 includes a polymer blend having approximately 85% Pellethane and approximately 15% Pebax, a mold diameter of approximately 32 mm, a design hoop stress of approximately 22,000 psi, a design burst pressure of approximately 18 psi, a tubing expansion ratio of approximately 6.8, a tubing design inner diameter of approximately 0.1853 inch, and a tubing design outer diameter of approximately 0.2052 inch.

Balloon 2 includes 100% Pellathane, a mold diameter of approximately 32 mm, a design hoop stress of approximately 12,000 psi, a design burst pressure of approximately 14 psi, a tubing expansion ratio of approximately 7.0, a tubing design inner diameter of approximately 0.2100 inch, and a tubing design outer diameter of approximately 0.2260 inch.

Balloon 3 includes 100% Pebax 6333D, a mold diameter of approximately 32 mm, a design hoop stress of approximately 30,000 psi, a design burst pressure of approximately 25 psi, a tubing expansion ratio of approximately 6.0, a tubing design inner diameter of approximately 0.1800 inch, and a tubing design outer diameter of approximately 0.1988 inch.

It is understood that the three cryogenic balloons 236 included in FIG. 3 are non-exclusive, representative examples of cryogenic balloons 236, and are not intended to be limiting in any manner of the specific materials that can be used to form the cryogenic balloon 236.

Referring again to FIG. 3, Balloon 1 can have a nominal outer diameter 239 of approximately 28.8 mm at a nominal working balloon pressure of approximately 2.5 psig. In Balloon 1, the nominal outer diameter 239 can be increased to approximately 33.4 mm at an inflation pressure of approximately 7.5 psig, or an increase of approximately 5.0 psi. In other words, the outer diameter 239 of Balloon 1 can be increased (or decreased) by approximately 4.6 mm with a change in inflation pressure of approximately 5.0 psi. Stated another way, for Balloon 1, the ratio of the change in inflation pressure (in psi) to the change in outer diameter 239 (in mm) is approximately 1.087:1. Further, in this embodiment, Balloon 1 exhibits a ratio of outer diameter 239 (in mm) to inflation pressure (in psig) of approximately 11.52:1 at 2.5 psig, and approximately 4.45:1 at 7.5 psig.

Balloon 2 can have a nominal outer diameter 239 of approximately 25.0 mm at a nominal working balloon pressure of approximately 2.5 psig. In Balloon 2, the nominal outer diameter 239 can be increased to approximately 32.9 mm at an inflation pressure of approximately 7.5 psig, or an increase of approximately 5.0 psi. In other words, the outer diameter 239 of Balloon 2 can be increased (or decreased) by approximately 7.9 mm with a change in inflation pressure of approximately 5.0 psi. Stated another way, for Balloon 2, the ratio of the change in inflation pressure (in psi) to the change in outer diameter 239 (in mm) is approximately 0.633:1. Further, in this embodiment, Balloon 2 exhibits a ratio of outer diameter 239 (in mm) to inflation pressure (in psig) of approximately 10:1 at 2.5 psig, and approximately 4.39:1 at 7.5 psig.

Balloon 3 can have a nominal outer diameter 239 of approximately 28.7 mm at a nominal working balloon pressure of approximately 2.5 psig. In Balloon 3, the nominal outer diameter 239 can be increased to approximately 29.9 mm at an inflation pressure of approximately 7.5 psig, or an increase of approximately 5.0 psi. In other words, the outer diameter 239 of Balloon 3 can be increased (or decreased) by approximately 1.2 mm with a change in inflation pressure of approximately 5.0 psi. Stated another way, for Balloon 3, the ratio of the change in inflation pressure (in psi) to the change in outer diameter 239 (in mm) is approximately 4.167:1. Further, in this embodiment, Balloon 3 exhibits a ratio of outer diameter 239 (in mm) to inflation pressure (in psig) of approximately 11.48:1 at 2.5 psig, and approximately 3.99:1 at 7.5 psig.

In other non-exclusive alternative embodiments, the materials used to form the cryogenic balloon 236 can be adjusted so that the ratio of the change in inflation pressure (in psi) to the change in outer diameter 239 (in mm) can be less than approximately 10:1, 9:1, 8:1, 7:1, 6:1, 5:1, 4:1, 3:1, 2:1, 1:1, 3:2, 1:2, 1:3 or 1:4. Additionally, or in the alternative, in certain embodiments, the ratio of outer diameter 239 (in mm) to inflation pressure (in psig) can be greater than approximately 20:1, 15:1, 12:1, 10:1, 8:1, 7:1, 6:1, 5:1, 4:1 or 3:1.

It is recognized that other materials or combinations of materials for cryogenic balloons 236 can yield other outer diameters 239 and inflation pressure operating ranges which offer a range of sizes within a therapeutic window of energy delivery.

It is understood that although a number of different embodiments of the intravascular catheter system 210 and/or the balloon catheter 218 have been illustrated and described herein, one or more features of any one embodiment can be combined with one or more features of one or more of the other embodiments, provided that such combination satisfies the intent of the present invention.

While a number of exemplary aspects and embodiments of the intravascular catheter system 210 and/or the balloon catheter 218 have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

I claim:

1. A balloon catheter for an intravascular catheter system, the balloon catheter comprising a cryogenic balloon assembly including an inner balloon and an outer balloon, the outer balloon formed from a blend of 85% polyurethane and 15% polyamide block copolymer, the cryogenic balloon assembly configured to have a maximum outer diameter at an inflation pressure, and wherein the cryogenic balloon assembly is configured such that, in operation, a ratio of a change in the inflation pressure (in psig) to a change in the maximum outer diameter is between 1.087:1 and 2:1, wherein the inner balloon and the outer balloon are configured such that upon inflation of the inner balloon, a portion of the inner balloon expands against a portion of the outer balloon, such that the outer balloon is inflated simultaneously with the inner balloon.

2. The balloon catheter of claim 1, wherein the cryogenic balloon assembly is configured such that, in operation, a ratio of the maximum outer diameter (in mm) of the cryogenic balloon assembly to inflation pressure (in psig) is greater than approximately 3:1.

3. The balloon catheter of claim 2, wherein the cryogenic balloon assembly is configured such that, in operation, a ratio of the maximum outer diameter (in mm) of the cryogenic balloon assembly to inflation pressure (in psig) is greater than approximately 5:1.

4. The balloon catheter of claim 1, further comprising a catheter shaft, and wherein a first end of the cryogenic balloon assembly is bonded to a distal end of the catheter shaft.

5. The balloon catheter of claim 4, wherein the first end of the cryogenic balloon assembly is heat-bonded to the distal end of the catheter shaft.

6. The balloon catheter of claim 5, further comprising a guidewire lumen disposed within the catheter shaft.

7. The balloon catheter of claim 6, wherein a second end of the cryogenic balloon assembly is bonded to a distal end of the guidewire lumen.

8. The balloon catheter of claim 7, wherein the second end of the cryogenic balloon assembly is heat-bonded to the distal end of the guidewire lumen.

9. The balloon catheter of claim 8, wherein the cryogenic balloon assembly is configured such that the maximum outer diameter is 28.8 mm when the inflation pressure is 2.5 psig, and the maximum outer diameter is 33.4 mm when the inflation pressure is 7.5 psig.

10. The balloon catheter of claim 8, wherein the cryogenic balloon assembly is configured such that the maximum outer diameter increases by approximately 4.6 mm with an increase in the inflation pressure of about 5.0 psig.

11. A cryoablation balloon catheter for treating cardiac arrhythmias in a patient, the cryoablation balloon catheter comprising:
a catheter shaft extending from a shaft proximal end to a shaft distal end, the catheter shaft configured to be advanced over a guidewire and positioned in a circulatory system of the patient;
a guidewire lumen extending beyond the shaft distal end to a guidewire lumen distal end, the guidewire lumen configured to be advanced over a guidewire such that the guidewire lumen distal end is positioned in a pulmonary vein ostium of the patient;
a handle assembly coupled to the proximal end of the catheter shaft, the handle assembly configured couple to a cryogenic fluid source; and
a balloon assembly having a balloon assembly proximal end heat-bonded to the catheter shaft and a balloon assembly distal end heat-bonded to the guidewire lumen such that a portion of the guidewire lumen extends distally from the balloon assembly distal end, the balloon assembly including an inner balloon and an outer balloon, the outer balloon formed from a blend of 85% Pellethane and 15% PEBAX by weight;
wherein the inner balloon and the outer balloon are configured such that upon inflation of the inner balloon, a portion of the inner balloon expands against a portion of the outer balloon, such that inflation of the inner balloon causes inflation of the outer balloon;
wherein the balloon assembly is configured to form a seal with the pulmonary vein ostium of the patient and is configured to have a first outer diameter at a first inflation pressure and a second outer diameter at a second inflation pressure, such that the ratio of a pressure change between the first inflation pressure and the second inflation pressure (in psig) and a diameter change between the first outer diameter and the second outer diameter is between 1.087:1 and 2:1.

12. The cryoablation balloon catheter of claim 11 further comprising a lubricious biocompatible material disposed between the inner balloon and the outer balloon, so as to reduce friction between the two balloons during inflation.

* * * * *